(12) United States Patent
Northrop et al.

(10) Patent No.: US 8,795,202 B2
(45) Date of Patent: Aug. 5, 2014

(54) GUIDEWIRES AND METHODS FOR MAKING AND USING THE SAME

(75) Inventors: Clay Northrop, Salt Lake City, UT (US); Ted Layman, Park City, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 135 days.

(21) Appl. No.: 13/365,886

(22) Filed: Feb. 3, 2012

(65) Prior Publication Data

US 2012/0203207 A1 Aug. 9, 2012

Related U.S. Application Data

(60) Provisional application No. 61/439,736, filed on Feb. 4, 2011.

(51) Int. Cl.
*A61B 5/00* (2006.01)
(52) U.S. Cl.
USPC .......................................................... 600/585
(58) Field of Classification Search
USPC .......................................................... 600/585
See application file for complete search history.

(56) References Cited

U.S. PATENT DOCUMENTS

| | | | |
|---|---|---|---|
| 1,553,227 A | 9/1925 | Anton et al. |
| 1,866,888 A | 7/1932 | Hawley |
| 2,275,827 A | 3/1942 | Plensler |
| 2,413,805 A | 1/1947 | Vickers |
| 2,441,166 A | 5/1948 | Raspert |
| 2,561,890 A | 7/1951 | Stoddard |
| 2,722,614 A | 11/1955 | Fryklund |
| 2,857,536 A | 10/1958 | Light |
| 2,864,017 A | 12/1958 | Waltscheff |
| 2,871,793 A | 2/1959 | Michie et al. |
| 3,249,776 A | 5/1966 | Anderson et al. |
| 3,322,984 A | 5/1967 | Anderson |
| 3,334,253 A | 8/1967 | Hill |
| 3,363,470 A | 1/1968 | Yavne |
| 3,452,227 A | 6/1969 | Welch |
| 3,452,742 A | 7/1969 | Muller |
| 3,463,953 A | 8/1969 | Maxwell |
| 3,512,019 A | 5/1970 | Durand |
| 3,544,868 A | 12/1970 | Bates |
| 3,625,200 A | 12/1971 | Muller |
| 3,686,990 A | 8/1972 | Margolien |

(Continued)

FOREIGN PATENT DOCUMENTS

| | | |
|---|---|---|
| DE | 4302693 A1 | 8/1994 |
| EP | 0215173 | 3/1987 |

(Continued)

OTHER PUBLICATIONS

H.A. Rothbart, "Helical Compression Springs", Mechanical Design and Systems Handbook, 1964, p. 33-13 (one sheet).

*Primary Examiner* — Max Hindenburg
(74) *Attorney, Agent, or Firm* — Seager, Tufte & Wickhem, LLC

(57) ABSTRACT

Medical devices and methods for making and using the same are disclosed. An example medical device may include a guidewire. The guidewire may include a core wire having a distal portion. A tubular member may be disposed over the distal portion. The tubular member may have a plurality of slots formed therein. A polymeric member may be disposed along an outer surface of the tubular member. The polymeric member may have an uneven outer surface.

18 Claims, 7 Drawing Sheets

(56) References Cited

U.S. PATENT DOCUMENTS

| | | | |
|---|---|---|---|
| 3,841,308 A | 10/1974 | Tate | |
| 3,890,977 A | 6/1975 | Wilson | |
| 3,906,938 A | 9/1975 | Fleischhacker | |
| 3,973,556 A * | 8/1976 | Fleischhacker et al. | 600/585 |
| 4,000,672 A | 1/1977 | Sitterer et al. | |
| 4,003,369 A | 1/1977 | Heilman et al. | |
| 4,020,829 A | 5/1977 | Willson et al. | |
| 4,142,119 A | 2/1979 | Madey | |
| 4,215,703 A | 8/1980 | Wilson | |
| 4,330,725 A | 5/1982 | Hintz | |
| 4,425,919 A | 1/1984 | Alston, Jr. et al. | |
| 4,476,754 A | 10/1984 | Ducret | |
| 4,482,828 A | 11/1984 | Vergues et al. | |
| 4,538,622 A | 9/1985 | Samson et al. | |
| 4,545,390 A | 10/1985 | Leary | |
| 4,563,181 A | 1/1986 | Wijayarathna et al. | |
| 4,574,670 A | 3/1986 | Johnson | |
| 4,580,551 A | 4/1986 | Siegmund et al. | |
| 4,583,404 A | 4/1986 | Bernard et al. | |
| 4,635,270 A | 1/1987 | Gürs | |
| 4,665,906 A | 5/1987 | Jervis | |
| 4,676,249 A | 6/1987 | Arenas et al. | |
| 4,721,117 A | 1/1988 | Mar et al. | |
| 4,737,153 A | 4/1988 | Shimamura et al. | |
| 4,763,647 A | 8/1988 | Gambale | |
| 4,774,949 A | 10/1988 | Fogarty | |
| 4,781,092 A | 11/1988 | Gaiser | |
| 4,781,186 A | 11/1988 | Simpson et al. | |
| 4,786,220 A | 11/1988 | Fildes et al. | |
| 4,790,331 A | 12/1988 | Okada et al. | |
| 4,800,890 A | 1/1989 | Cramer | |
| 4,811,743 A | 3/1989 | Stevens | |
| 4,827,941 A | 5/1989 | Taylor et al. | |
| 4,831,858 A | 5/1989 | Yoshizawa | |
| 4,832,047 A | 5/1989 | Sepetka et al. | |
| 4,846,186 A | 7/1989 | Box et al. | |
| 4,846,193 A | 7/1989 | Tremulis et al. | |
| 4,867,173 A | 9/1989 | Leoni | |
| 4,875,489 A | 10/1989 | Messner et al. | |
| 4,884,579 A | 12/1989 | Engelson | |
| 4,911,148 A | 3/1990 | Sosnowski et al. | |
| 4,917,102 A | 4/1990 | Miller et al. | |
| 4,922,164 A | 5/1990 | Jacobsen et al. | |
| 4,922,777 A | 5/1990 | Kawabata | |
| 4,932,959 A | 6/1990 | Horzewski et al. | |
| 4,934,380 A | 6/1990 | Toledo | |
| 4,953,553 A | 9/1990 | Tremulis | |
| 4,954,022 A | 9/1990 | Underwood et al. | |
| 4,955,384 A | 9/1990 | Taylor et al. | |
| 4,955,862 A | 9/1990 | Sepetka | |
| 4,960,410 A | 10/1990 | Pinchuk | |
| 4,964,409 A | 10/1990 | Tremulis | |
| 4,966,163 A | 10/1990 | Kraus et al. | |
| 4,968,306 A | 11/1990 | Huss et al. | |
| 4,973,321 A | 11/1990 | Michelson | |
| 4,985,022 A | 1/1991 | Fearnot et al. | |
| 4,989,608 A | 2/1991 | Ratner | |
| 4,990,143 A | 2/1991 | Sheridan | |
| 4,994,069 A | 2/1991 | Ritchart et al. | |
| 4,998,923 A | 3/1991 | Samson et al. | |
| 5,007,434 A | 4/1991 | Doyle et al. | |
| 5,009,137 A | 4/1991 | Dannatt | |
| 5,040,543 A | 8/1991 | Badera et al. | |
| 5,050,606 A | 9/1991 | Tremulis | |
| 5,052,404 A | 10/1991 | Hodgson | |
| 5,059,177 A | 10/1991 | Alcebo et al. | |
| 5,063,935 A | 11/1991 | Gamble | |
| 5,065,769 A | 11/1991 | De Toledo | |
| 5,095,915 A * | 3/1992 | Engelson | 600/585 |
| 5,106,455 A | 4/1992 | Jacobsen et al. | |
| 5,109,830 A | 5/1992 | Cho | |
| 5,125,395 A | 6/1992 | Adair | |
| 5,135,531 A | 8/1992 | Shiber | |
| 5,144,959 A | 9/1992 | Gambale et al. | |
| 5,147,317 A | 9/1992 | Shank et al. | |
| 5,181,668 A | 1/1993 | Tsuji et al. | |
| 5,205,830 A | 4/1993 | Dassa et al. | |
| 5,211,183 A | 5/1993 | Wilson | |
| 5,228,441 A | 7/1993 | Lundquist | |
| 5,228,453 A | 7/1993 | Sepetka | |
| 5,238,004 A | 8/1993 | Sahatjian et al. | |
| 5,242,759 A | 9/1993 | Hall | |
| 5,243,996 A | 9/1993 | Hall | |
| 5,250,069 A | 10/1993 | Nobuyoshi et al. | |
| 5,254,106 A | 10/1993 | Feaster | |
| 5,254,107 A | 10/1993 | Soltesz | |
| 5,256,144 A | 10/1993 | Kraus et al. | |
| 5,257,974 A | 11/1993 | Cox | |
| 5,259,393 A | 11/1993 | Corso, Jr. et al. | |
| 5,267,979 A | 12/1993 | Appling et al. | |
| 5,267,982 A | 12/1993 | Sylvanowicz | |
| 5,279,562 A | 1/1994 | Sirhan et al. | |
| 5,284,128 A | 2/1994 | Hart | |
| 5,300,032 A | 4/1994 | Hibbs et al. | |
| 5,304,131 A | 4/1994 | Paskar | |
| 5,306,252 A | 4/1994 | Yutori et al. | |
| 5,308,435 A | 5/1994 | Ruggles et al. | |
| 5,315,906 A | 5/1994 | Ferenczi et al. | |
| 5,315,996 A | 5/1994 | Lundquist | |
| 5,318,529 A | 6/1994 | Kontos | |
| 5,322,064 A | 6/1994 | Lundquist | |
| 5,329,923 A | 7/1994 | Lundquist | |
| 5,333,620 A | 8/1994 | Moutafis et al. | |
| 5,334,145 A | 8/1994 | Lundquist et al. | |
| 5,336,205 A | 8/1994 | Zenzen et al. | |
| 5,341,818 A | 8/1994 | Abrams et al. | |
| 5,345,937 A | 9/1994 | Middleman et al. | |
| 5,345,945 A | 9/1994 | Hodgson et al. | |
| 5,354,623 A | 10/1994 | Hall | |
| 5,358,493 A | 10/1994 | Schweich et al. | |
| 5,358,796 A | 10/1994 | Nakamura et al. | |
| 5,365,942 A | 11/1994 | Shank | |
| 5,365,943 A | 11/1994 | Jansen | |
| 5,368,049 A | 11/1994 | Raman et al. | |
| 5,368,564 A | 11/1994 | Savage | |
| 5,368,661 A | 11/1994 | Nakamura et al. | |
| 5,376,084 A | 12/1994 | Bacich et al. | |
| 5,381,782 A | 1/1995 | DeLaRama et al. | |
| 5,406,960 A | 4/1995 | Corso, Jr. | |
| 5,409,015 A | 4/1995 | Palermo | |
| 5,411,476 A | 5/1995 | Abrams | |
| 5,425,723 A | 6/1995 | Wang | |
| 5,437,288 A * | 8/1995 | Schwartz et al. | 600/585 |
| 5,438,993 A | 8/1995 | Lynch et al. | |
| 5,439,000 A | 8/1995 | Gunderson et al. | |
| 5,441,483 A | 8/1995 | Avitall | |
| 5,441,489 A | 8/1995 | Utsumi et al. | |
| 5,443,907 A * | 8/1995 | Slaikeu et al. | 428/375 |
| 5,447,812 A | 9/1995 | Fukuda et al. | |
| 5,454,787 A | 10/1995 | Lundquist | |
| 5,460,187 A | 10/1995 | Daigle et al. | |
| 5,470,330 A | 11/1995 | Goldenberg et al. | |
| 5,476,701 A | 12/1995 | Berger | |
| 5,477,856 A | 12/1995 | Lundquist | |
| 5,496,294 A | 3/1996 | Hergenrother et al. | |
| 5,497,785 A | 3/1996 | Viera | |
| 5,507,301 A | 4/1996 | Wasicek et al. | |
| 5,507,729 A | 4/1996 | Lindenberg et al. | |
| 5,507,751 A | 4/1996 | Goode et al. | |
| 5,507,766 A | 4/1996 | Kugo et al. | |
| 5,514,128 A | 5/1996 | Hillsman et al. | |
| 5,520,194 A | 5/1996 | Miyata et al. | |
| 5,520,645 A | 5/1996 | Imran et al. | |
| 5,531,719 A | 7/1996 | Takahashi | |
| 5,533,985 A | 7/1996 | Wang | |
| 5,546,958 A | 8/1996 | Thorud et al. | |
| 5,551,444 A | 9/1996 | Finlayson | |
| 5,554,139 A | 9/1996 | Okajima | |
| 5,562,619 A | 10/1996 | Mirarchi et al. | |
| 5,569,197 A | 10/1996 | Helmus et al. | |
| 5,569,200 A | 10/1996 | Umeno et al. | |
| 5,569,218 A | 10/1996 | Berg | |
| 5,571,073 A | 11/1996 | Castillo | |
| 5,573,520 A | 11/1996 | Schwartz et al. | |

(56) References Cited

U.S. PATENT DOCUMENTS

| | | | |
|---|---|---|---|
| 5,584,821 A | 12/1996 | Hobbs et al. |
| 5,599,326 A | 2/1997 | Carter |
| 5,599,492 A | 2/1997 | Engelson |
| 5,601,539 A | 2/1997 | Corso, Jr. |
| 5,605,162 A | 2/1997 | Mirzaee et al. |
| 5,605,543 A | 2/1997 | Swanson |
| 5,622,184 A | 4/1997 | Ashby et al. |
| 5,630,806 A | 5/1997 | Inagaki et al. |
| 5,637,089 A | 6/1997 | Abrams et al. |
| 5,656,011 A | 8/1997 | Uihlein et al. |
| 5,658,264 A | 8/1997 | Samson et al. |
| 5,664,580 A | 9/1997 | Erickson et al. |
| 5,666,968 A | 9/1997 | Imran et al. |
| 5,666,969 A | 9/1997 | Urick et al. |
| 5,669,926 A | 9/1997 | Aust et al. |
| 5,676,659 A | 10/1997 | McGurk |
| 5,676,697 A | 10/1997 | McDonald |
| 5,682,894 A | 11/1997 | Orr et al. |
| 5,683,370 A | 11/1997 | Luther et al. |
| 5,690,120 A | 11/1997 | Jacobsen et al. |
| 5,720,300 A | 2/1998 | Fagan et al. |
| 5,722,609 A | 3/1998 | Murakami |
| 5,728,063 A | 3/1998 | Preissman et al. |
| 5,741,429 A | 4/1998 | Donadio, III et al. |
| 5,746,701 A * | 5/1998 | Noone ................... 600/585 |
| 5,769,830 A | 6/1998 | Parker |
| 5,772,609 A | 6/1998 | Nguyen et al. |
| 5,782,809 A | 7/1998 | Umeno et al. |
| 5,788,653 A | 8/1998 | Lorenzo |
| 5,788,654 A | 8/1998 | Schwager |
| 5,788,707 A | 8/1998 | Del Toro et al. |
| 5,792,124 A | 8/1998 | Horrigan et al. |
| 5,797,856 A | 8/1998 | Frisbie et al. |
| 5,800,454 A | 9/1998 | Jacobsen et al. |
| 5,807,075 A | 9/1998 | Jacobsen et al. |
| 5,807,249 A | 9/1998 | Qin et al. |
| 5,810,885 A | 9/1998 | Zinger |
| 5,813,996 A | 9/1998 | St. Germain et al. |
| 5,827,225 A | 10/1998 | Ma Schwab |
| 5,827,242 A | 10/1998 | Follmer et al. |
| 5,833,632 A | 11/1998 | Jacobsen et al. |
| 5,836,926 A | 11/1998 | Peterson et al. |
| 5,840,046 A * | 11/1998 | Deem ................... 600/585 |
| 5,843,050 A | 12/1998 | Jones et al. |
| 5,843,244 A | 12/1998 | Pelton et al. |
| 5,851,203 A | 12/1998 | van Muiden |
| 5,895,378 A | 4/1999 | Nita |
| 5,897,537 A | 4/1999 | Berg et al. |
| 5,902,254 A | 5/1999 | Magram |
| 5,902,290 A | 5/1999 | Peacock, III et al. |
| 5,902,499 A | 5/1999 | Richerzhagen |
| 5,904,657 A | 5/1999 | Unsworth et al. |
| 5,906,618 A | 5/1999 | Larson, III |
| 5,911,715 A | 6/1999 | Berg et al. |
| 5,911,717 A | 6/1999 | Jacobsen et al. |
| 5,916,177 A | 6/1999 | Schwager |
| 5,916,178 A | 6/1999 | Noone |
| 5,916,194 A | 6/1999 | Jacobsen et al. |
| 5,931,830 A | 8/1999 | Jacobsen et al. |
| 5,935,108 A | 8/1999 | Katoh et al. |
| 5,947,940 A | 9/1999 | Beisel |
| 5,951,539 A | 9/1999 | Nita et al. |
| 5,955,640 A | 9/1999 | Paludetto et al. |
| 5,971,975 A | 10/1999 | Mills et al. |
| 5,980,471 A | 11/1999 | Jafari |
| 5,997,487 A | 12/1999 | Kolehmainen et al. |
| 6,001,068 A | 12/1999 | Uchino et al. |
| 6,004,279 A | 12/1999 | Crowley et al. |
| 6,007,478 A | 12/1999 | Siess et al. |
| 6,014,919 A | 1/2000 | Jacobsen et al. |
| 6,017,319 A | 1/2000 | Jacobsen et al. |
| 6,022,343 A | 2/2000 | Johnson et al. |
| 6,022,369 A | 2/2000 | Jacobsen et al. |
| 6,024,730 A | 2/2000 | Pagan |
| 6,027,461 A | 2/2000 | Walker et al. |
| 6,042,553 A | 3/2000 | Solar et al. |
| 6,045,547 A | 4/2000 | Ren et al. |
| 6,048,339 A | 4/2000 | Zirps et al. |
| 6,056,702 A | 5/2000 | Lorenzo |
| 6,063,101 A | 5/2000 | Jacobsen et al. |
| 6,063,200 A | 5/2000 | Jacobsen et al. |
| 6,066,361 A | 5/2000 | Jacobsen et al. |
| 6,071,305 A | 6/2000 | Brown et al. |
| 6,106,485 A | 8/2000 | McMahon |
| 6,106,488 A | 8/2000 | Fleming et al. |
| 6,139,510 A | 10/2000 | Palermo |
| 6,165,292 A | 12/2000 | Abrams et al. |
| 6,171,296 B1 | 1/2001 | Chow |
| 6,183,410 B1 | 2/2001 | Jacobsen et al. |
| 6,193,686 B1 | 2/2001 | Estrada et al. |
| 6,197,014 B1 | 3/2001 | Samson et al. |
| 6,203,485 B1 | 3/2001 | Urick |
| RE37,148 E | 4/2001 | Shank |
| 6,214,042 B1 | 4/2001 | Jacobsen et al. |
| 6,228,073 B1 | 5/2001 | Noone et al. |
| 6,248,082 B1 | 6/2001 | Jafari |
| 6,251,085 B1 * | 6/2001 | Tezuka ................... 600/585 |
| 6,251,092 B1 | 6/2001 | Qin et al. |
| 6,254,549 B1 | 7/2001 | Ramzipoor |
| 6,260,458 B1 | 7/2001 | Jacobsen et al. |
| 6,273,404 B1 | 8/2001 | Holman et al. |
| 6,273,876 B1 | 8/2001 | Klima et al. |
| 6,273,879 B1 | 8/2001 | Keith et al. |
| 6,290,656 B1 | 9/2001 | Boyle et al. |
| 6,296,616 B1 | 10/2001 | McMahon |
| 6,296,631 B2 | 10/2001 | Chow |
| 6,302,870 B1 | 10/2001 | Jacobsen et al. |
| 6,325,790 B1 | 12/2001 | Trotta |
| 6,338,725 B1 | 1/2002 | Hermann et al. |
| 6,346,091 B1 | 2/2002 | Jacobsen et al. |
| 6,352,515 B1 | 3/2002 | Anderson et al. |
| 6,355,005 B1 | 3/2002 | Powell et al. |
| 6,355,027 B1 | 3/2002 | Le et al. |
| 6,368,315 B1 | 4/2002 | Gillis et al. |
| 6,368,316 B1 | 4/2002 | Jansen et al. |
| 6,375,628 B1 | 4/2002 | Zadno-Azizi et al. |
| 6,375,774 B1 | 4/2002 | Lunn et al. |
| 6,379,369 B1 | 4/2002 | Abrams et al. |
| 6,383,146 B1 | 5/2002 | Klint |
| 6,390,993 B1 | 5/2002 | Cornish et al. |
| 6,398,758 B1 | 6/2002 | Jacobsen et al. |
| 6,428,489 B1 | 8/2002 | Jacobsen et al. |
| 6,428,512 B1 | 8/2002 | Anderson et al. |
| 6,431,039 B1 | 8/2002 | Jacobsen et al. |
| 6,440,088 B1 | 8/2002 | Jacobsen |
| 6,478,778 B1 | 11/2002 | Jacobsen et al. |
| 6,488,637 B1 | 12/2002 | Eder et al. |
| 6,491,648 B1 | 12/2002 | Cornish et al. |
| 6,491,671 B1 | 12/2002 | Larson, III et al. |
| 6,503,244 B2 | 1/2003 | Hayman |
| 6,508,803 B1 | 1/2003 | Horikawa et al. |
| 6,524,301 B1 | 2/2003 | Wilson et al. |
| 6,530,934 B1 | 3/2003 | Jacobsen et al. |
| 6,547,779 B2 | 4/2003 | Levine et al. |
| 6,553,880 B2 | 4/2003 | Jacobsen et al. |
| 6,556,873 B1 | 4/2003 | Smits |
| 6,579,246 B2 * | 6/2003 | Jacobsen et al. ............ 600/585 |
| 6,602,207 B1 | 8/2003 | Mann et al. |
| 6,602,280 B2 | 8/2003 | Chobotov |
| 6,610,046 B1 | 8/2003 | Usami et al. |
| 6,623,448 B2 | 9/2003 | Slater |
| 6,636,758 B2 | 10/2003 | Sanchez et al. |
| 6,638,266 B2 | 10/2003 | Wilson et al. |
| 6,652,508 B2 | 11/2003 | Griffin et al. |
| 6,673,025 B1 | 1/2004 | Richardson et al. |
| 6,682,493 B2 | 1/2004 | Mirigian |
| 6,689,120 B2 | 2/2004 | Gerdts |
| 6,702,762 B2 | 3/2004 | Jafari et al. |
| 6,712,826 B2 | 3/2004 | Lui |
| 6,730,095 B2 | 5/2004 | Olson, Jr. et al. |
| 6,749,560 B1 | 6/2004 | Konstorum et al. |
| 6,766,720 B1 | 7/2004 | Jacobsen et al. |
| 6,777,644 B2 | 8/2004 | Peacock, III et al. |
| 6,811,544 B2 | 11/2004 | Schaer |

(56) References Cited

U.S. PATENT DOCUMENTS

| | | |
|---|---|---|
| 6,837,898 B2 | 1/2005 | Boyle et al. |
| 6,866,642 B2 | 3/2005 | Kellerman et al. |
| 6,887,235 B2 | 5/2005 | O'Connor et al. |
| 6,918,882 B2 | 7/2005 | Skujins et al. |
| 6,997,937 B2 | 2/2006 | Jacobsen et al. |
| 7,001,369 B2 | 2/2006 | Griffin et al. |
| 7,071,197 B2 | 7/2006 | Leonardi et al. |
| 7,074,197 B2 | 7/2006 | Reynolds et al. |
| 7,153,277 B2 | 12/2006 | Skujins et al. |
| 7,169,118 B2 | 1/2007 | Reynolds et al. |
| 7,182,735 B2 | 2/2007 | Shireman et al. |
| 7,618,379 B2 | 11/2009 | Reynolds et al. |
| 7,708,704 B2 * | 5/2010 | Mitelberg et al. .............. 600/585 |
| 7,850,623 B2 | 12/2010 | Griffin et al. |
| 7,878,984 B2 * | 2/2011 | Jacobsen et al. .............. 600/585 |
| 7,905,913 B2 | 3/2011 | Chew et al. |
| 7,914,466 B2 | 3/2011 | Davis et al. |
| 7,955,272 B2 | 6/2011 | Rooney et al. |
| 7,989,042 B2 | 8/2011 | Obara et al. |
| 8,048,004 B2 | 11/2011 | Jacobsen et al. |
| 8,083,689 B2 | 12/2011 | Vrba |
| 8,113,916 B2 | 2/2012 | Miller et al. |
| 8,500,657 B2 * | 8/2013 | Brown .......................... 600/585 |
| 8,535,243 B2 * | 9/2013 | Shireman ...................... 600/585 |
| 2003/0009208 A1 | 1/2003 | Snyder et al. |
| 2003/0060732 A1 | 3/2003 | Jacobsen et al. |
| 2003/0069522 A1 | 4/2003 | Jacobsen et al. |
| 2003/0216668 A1 | 11/2003 | Howland et al. |
| 2004/0116831 A1 | 6/2004 | Vrba |
| 2004/0167437 A1 | 8/2004 | Sharrow et al. |
| 2004/0167441 A1 | 8/2004 | Reynolds et al. |
| 2004/0181176 A1 | 9/2004 | Jafari et al. |
| 2005/0115624 A1 | 6/2005 | Walak |
| 2006/0264904 A1 | 11/2006 | Kerby et al. |
| 2008/0021347 A1 | 1/2008 | Jacobsen et al. |
| 2008/0021348 A1 | 1/2008 | Jacobsen et al. |
| 2008/0021400 A1 | 1/2008 | Jacobsen et al. |
| 2008/0021401 A1 | 1/2008 | Jacobsen et al. |
| 2008/0021402 A1 | 1/2008 | Jacobsen et al. |
| 2008/0021403 A1 | 1/2008 | Jacobsen et al. |
| 2008/0021405 A1 | 1/2008 | Jacobsen et al. |
| 2008/0021406 A1 | 1/2008 | Jacobsen et al. |
| 2008/0021407 A1 | 1/2008 | Jacobsen et al. |
| 2008/0021408 A1 | 1/2008 | Jacobsen et al. |
| 2008/0064989 A1 | 3/2008 | Chen et al. |
| 2008/0077119 A1 | 3/2008 | Snyder et al. |
| 2009/0043283 A1 | 2/2009 | Turnland et al. |
| 2009/0043372 A1 | 2/2009 | Northrop et al. |
| 2009/0118675 A1 | 5/2009 | Czyscon et al. |
| 2009/0177185 A1 | 7/2009 | Northrop |
| 2009/0254000 A1 | 10/2009 | Layman et al. |
| 2010/0063479 A1 | 3/2010 | Merdan et al. |

FOREIGN PATENT DOCUMENTS

| | | |
|---|---|---|
| EP | 0377453 | 7/1990 |
| EP | 0498476 A1 | 8/1992 |
| EP | 0747089 A2 | 12/1996 |
| EP | 0778039 | 6/1997 |
| EP | 0937481 | 8/1999 |
| EP | 0790066 B1 | 4/2000 |
| EP | 0608853 B1 | 4/2003 |
| GB | 2257269 | 1/1993 |
| JP | 58-8522 | 1/1983 |
| JP | 62-299277 | 12/1987 |
| JP | 1-135363 | 5/1989 |
| JP | 1-158936 | 6/1989 |
| JP | 2-107268 | 4/1990 |
| JP | 3-122850 | 12/1991 |
| JP | 4-061840 | 2/1992 |
| JP | 5-506806 | 10/1993 |
| JP | 5-309519 | 11/1993 |
| JP | 6-31749 | 4/1994 |
| JP | 6-63224 | 9/1994 |
| JP | 6-312313 | 11/1994 |
| JP | 7-124164 | 5/1995 |
| JP | 7-124263 | 5/1995 |
| JP | 7-136280 | 5/1995 |
| JP | 7148264 | 6/1995 |
| JP | 7037199 | 7/1995 |
| JP | 7185009 | 7/1995 |
| JP | 7275366 | 10/1995 |
| JP | 751067 | 11/1995 |
| JP | 8509141 | 10/1996 |
| JP | 8-317988 | 12/1996 |
| JP | 9-000164 | 4/1997 |
| JP | 9-276413 | 10/1997 |
| JP | 10-118193 | 5/1998 |
| JP | 2000-197704 A | 7/2000 |
| WO | WO 90/02520 | 3/1990 |
| WO | WO 94/06500 | 3/1994 |
| WO | WO 95/32834 | 12/1995 |
| WO | WO 96/38193 | 12/1996 |
| WO | WO 97/44086 | 11/1997 |
| WO | WO 99/11313 | 3/1999 |
| WO | WO 02/13682 | 2/2002 |
| WO | WO 2004/047899 | 6/2004 |
| WO | WO 2004/075726 A2 | 9/2004 |
| WO | WO 2009/143160 | 11/2009 |

* cited by examiner

GUIDEWIRES AND METHODS FOR MAKING AND USING THE SAME

CROSS-REFERENCE TO RELATED APPLICATION

This application claims the benefit of U.S. Provisional Application Ser. No. 61/439,736, filed Feb. 4, 2011, the entire disclosure of which is incorporated herein by reference.

FIELD OF THE INVENTION

The present invention pertains to medical devices, and methods for manufacturing medical devices. More particularly, the present invention pertains to elongated medical devices including a slotted tubular member and a polymeric member.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

Embodiments of the present disclosure provide design, material, manufacturing method, and use alternatives for medical devices and tubular members for use in medical devices. An example medical device may include a guidewire. The guidewire may include a core wire having a distal portion. A tubular member may be disposed over the distal portion. The tubular member may have a plurality of slots formed therein. A polymeric member may be disposed along an outer surface of the tubular member. The polymeric member may have an uneven outer surface.

Another example guidewire may include a core wire having a distal portion. A tubular member may be disposed over the distal portion. The tubular member may have a plurality of slots formed therein. The guidewire may also include a polymeric jacket having a first portion disposed along an outer surface of the tubular member and a second portion disposed within the tubular member. The first portion of the polymeric jacket may have an uneven outer surface.

Another example guidewire having an atraumatic distal tip may include a core wire having a distal portion. A polymer member disposed over the distal portion. The polymer member may include a polymer doped with a radiopaque material. The polymer member may form a distal tip for the guidewire. The distal tip may have an uneven outer surface. A nickel-titanium alloy tubular member may be disposed over the distal portion of the core wire. The tubular member may have a plurality of slots formed therein. At least a portion of the polymer member may be disposed along an exterior surface of the tubular member.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The devices and methods of the present disclosure may be more completely understood in consideration of the following detailed description of various embodiments in connection with the accompanying drawings, in which.

Figure 1:
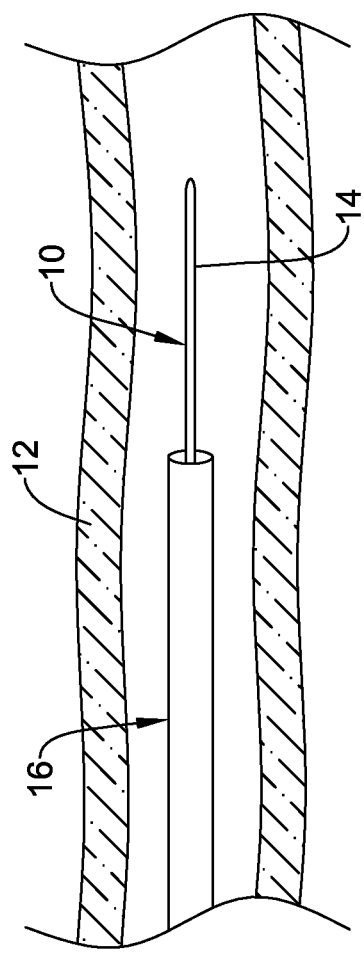
FIG. 1 is a plan view of an example medical device disposed in a blood vessel.

While the embodiments described herein are amenable to various modifications and alternative forms, specifics thereof have been shown by way of example in the drawings and will be described in detail. It should be understood, however, that the intention is not to limit the devices and methods to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a plan view of an example medical device 10, for example a guidewire, disposed in a blood vessel 12. Guidewire 10 may include a distal section 14 that may be generally configured for probing within the anatomy of a patient. Guidewire 10 may be used for intravascular procedures. For example, guidewire 10 may be used in conjunction with another medical device 16, which may take the form of a catheter, to treat and/or diagnose a medical condition. Of course, numerous other uses are known amongst clinicians for guidewires, catheters, and other similarly configured medical devices.

Figure 2:
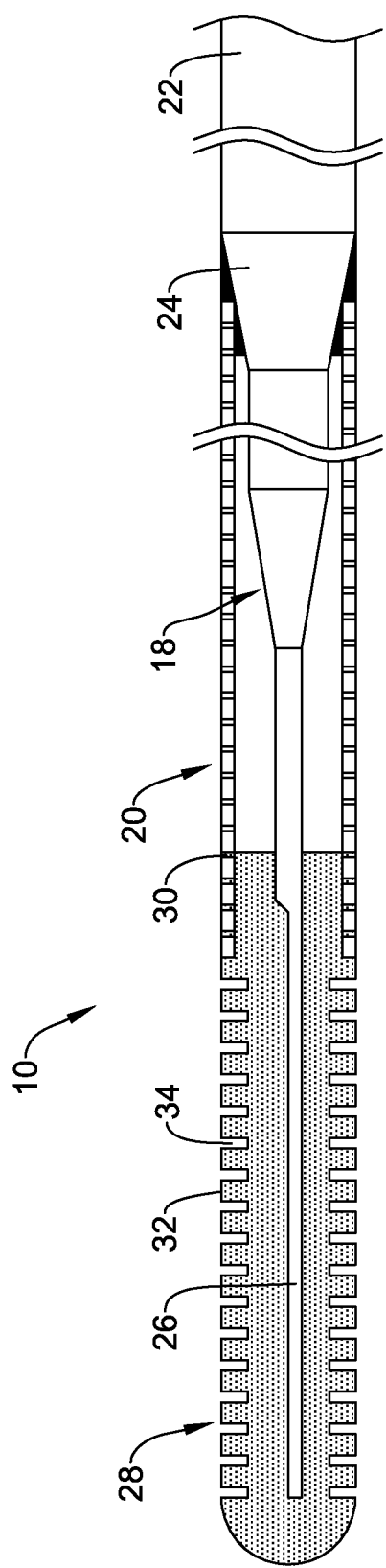
FIG. 2 is a partial cross-sectional side view of an example medical device.

FIG. 2 is a partial cross-sectional view of guidewire 10. It can be seen that guidewire 10 may include a core member or core wire 18 and a tubular member 20 disposed over at least a portion of core wire 18. Tubular member 20 may have a plurality of slots 30 formed therein. Core wire 18 may include a proximal section 22 and a distal section 24. A connector (not shown) may be disposed between and attach proximal section 22 to distal section 24. Alternatively, core wire 18 may be a unitary member without a connector.

Core wire 18 may include a flattened distal portion 26. Flattened portion 26 may define a shapeable structure (e.g., a shaping ribbon) that allows the distal end of guidewire 10 to be altered in shape. In at least some embodiments, flattened portion 26 is simply a flattened or stamped portion of core wire 18. In other embodiments, flattened portion 26 is a flattened member that is attached to core wire 18. In still other embodiments, core wire 18 may lack flattened portion 26 such that core wire 18 may be substantially round or otherwise unaltered at the distal end thereof.

A polymeric member 28 may be coupled to tubular member 20. As suggested by the name, polymeric member 28 may be made from a polymeric material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments, polymeric member 28 can be blended with a liquid crystal polymer (LCP), for example, up to about 6 wt-% LCP.

In some of these as well as other embodiments, polymeric member 28 may include a radiopaque material. In other words, polymeric member 28 may include a polymer loaded with radiopaque material. For example, polymeric member 28 or one or more discrete portions thereof may include about 50-95 wt-% or about 75-95 wt-% radiopaque material with the balance being polymeric. In some embodiments, the radiopaque material includes tungsten. Other materials and/or arrangements are contemplated. By virtue of including a radiopaque material in polymeric member 28, guidewire 10 may be manufactured without having additional radiopaque marker bands or coils coupled thereto, for example at the distal end of guidewire 10. In other embodiments, however, guidewire 10 may include such radiopaque structures.

In at least some embodiments, polymeric member 28 may extend distally from the distal end of tubular member 20. As such, polymeric member 28 may form and/or define the distal tip of guidewire 10. In other embodiments, a separate tip (e.g., a solder ball tip) may be attached to polymeric member 28. Polymeric member 28 may also include a lubricious material so as to improve the lubricity at, for example, the distal tip of guidewire 10. Polymeric member 28 may also extend proximally beyond a distal end of tubular member 20. Either or both of these arrangements may or may not include polymeric member 28 filling in some of slots 30 formed in tubular member 20.

Polymeric member 28 may have an uneven outer surface 32. For example, one or more slots, cuts, grooves, ribs, waves, or the like 34 may be formed in outer surface 32. The pattern may be regular in nature, random in nature, etc. Ribs 34 may be desirable for a number of reasons. For example, ribs 34 may increase the flexibility of guidewire 10, for example adjacent polymeric member 28. In addition, ribs 34 may help to provide polymeric member 28 and/or guidewire 10 with isotropic bending characteristics (e.g., by reducing the bending stiffness is essentially all directions), anisotropic bending characteristic (e.g., by reducing the bending stiffness in one or more directions), or both (e.g., along differing portions thereof).

The arrangement, pattern, and configuration of ribs 34 may vary in any of the manners discussed herein with respect to slots 30 of tubular member 20. For example, cuts 34 may be angled toward the distal end of polymeric member 28, angled toward the proximal end of polymeric member 28, be substantially normal to the longitudinal axis of polymeric member 28, be arranged in a spiral or helical pattern, be partially circumferential, extend about the full circumference of polymeric member 28, form a smooth surface, form a pebble-like or otherwise uneven or non-smooth surface, or a combination thereof. This may include mixtures of transverse or partially circumferential ribs 34 and circumferential ribs 34 as well as mixtures in the orientation and/or arrangement of ribs 34. Ribs 34 may extend about a portion of the circumference of polymeric member 28, may extend about the full circumference or more of polymeric member 28, or include combinations thereof. In at least some embodiments, ribs 34 may be arranged so as to provide essentially isotropic bending characteristics (e.g., flexibility in bending is essentially equal in all directions) to polymeric member 28 and/or guidewire 10. For example, ribs 34 may include a plurality of circumferential ribs 34 that facilitate equal bending in essentially all directions. Alternatively, ribs 34 may be arranged so as to provide essentially anisotropic bending characteristics (flexibility in bending differs depending on direction) to polymeric member 28 and/or guidewire 10. For example, ribs 34 may include a plurality of ribs 34 (e.g., partially circumferential) that are longitudinally aligned so as to define one or more preferred bending directions in directions that correspond to ribs 34. Numerous variations are contemplated including those disclosed in U.S. patent application Ser. No. 12/099,014, published as U.S. Patent Application Pub No. US 2009/0254000, the entire disclosure of which is herein incorporated by reference. These same arrangements and variations thereof may also be utilized, as appropriate, in any of the other embodiments disclosed herein.

Forming ribs 34 may include a suitable process. For example, ribs 34 may be formed via molding polymeric member 28. Alternatively, ribs 34 may be formed by grinding, cutting, or otherwise physically altering polymeric member 28. This may include laser cutting. Other processes are contemplated.

Polymeric member 28 may extend within and bond with tubular member 20 and/or core wire 18. This bond point may be the only location along the length of guidewire 10 where polymeric member 28, tubular member 20, and core wire 18 are all bonded together. Alternatively, other bond points may be utilized. In some embodiments, polymeric member 28 may "interlock" with tubular member 20 by virtue of being disposed within and filling some of slots 30. In other embodiments, another structure such as a coil, bushing, or the like (not shown) may be disposed within and enhance the bond between polymeric member 28, tubular member 20, and core wire 18. In addition, such a structure may help to center or otherwise maintain the desired alignment of core wire 18 within tubular member 20.

As indicated above, core wire 18 may include flattened distal portion 26. In at least some embodiments, ribs 34 are formed so that they are formed in the same plane as flattened distal portion 26. In other words, ribs 34 may be formed in polymeric member 28 so that they project inward in the same direction that core wire 18 is flattened so as to form flattened distal portion 26. Such a configuration may allow for enhanced shapeability and/or flexibility of guidewire 10. Other arrangement and configurations are contemplated for ribs 34 including arrangements that may or may not be relative to flattened distal portion 26.

FIG. 2 illustrates polymeric member 28 as being a solid structure that essentially encapsulates core wire 18 (e.g., flattened distal portion 26). Such an arrangement, however, is not intended to be limiting. For example, some embodiments are contemplated where polymeric member 28 is a tubular structure that may leave a space or gap between portions of polymeric member 28 and core wire 18. In still other embodiments, polymeric member 28 may be a structure that includes portions that essentially encapsulate core wire 18 and portions are spaced from core wire 18. Numerous alternative variations are contemplated.

Figure 3:
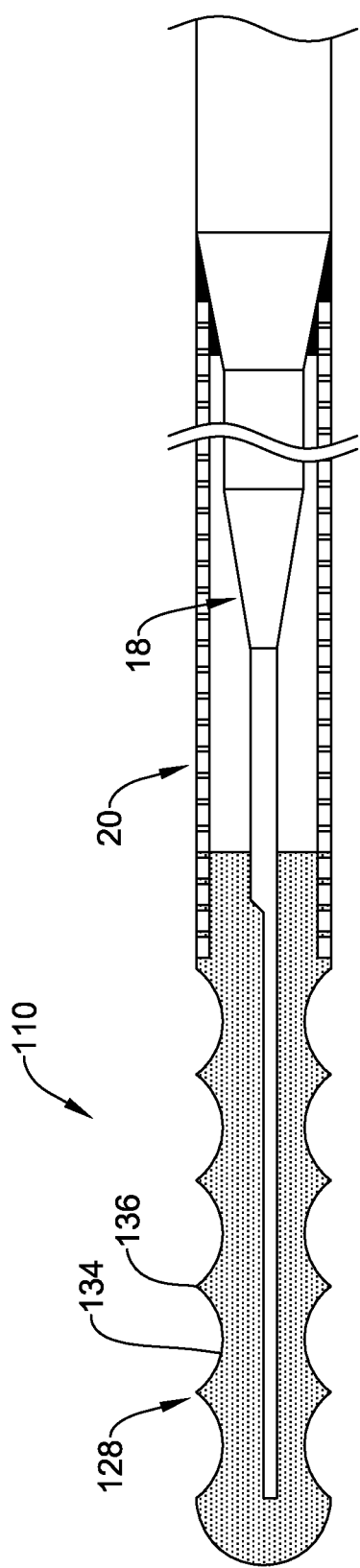
FIG. 3 is a partial cross-sectional side view of another example medical device.

FIG. 3 illustrates another guidewire 110 that may be similar in form and function to other guidewires disclosed herein. Guidewire 110 may include polymeric member 128 having a plurality of circumferential grooves 134 formed therein that define an uneven outer surface for polymeric member 128. The cross-sectional view of grooves 134 (as shown in FIG. 3) may appear as a series of concave dents or inward projections. The form or configuration of grooves 134, however, may vary vastly. In at least some embodiments, grooves 134 may provide a three-dimensional structural array along the exterior of polymeric member 128. A plurality of peaks 136 or projections may be defined between longitudinally-adjacent grooves 134. While grooves 134 are shown in FIG. 3 as being circumferential, this is not intended to be limiting as guidewires are contemplated that include one or more partially circumferential grooves. The same may be true in any of the other embodiments disclosed herein.

Figure 4:
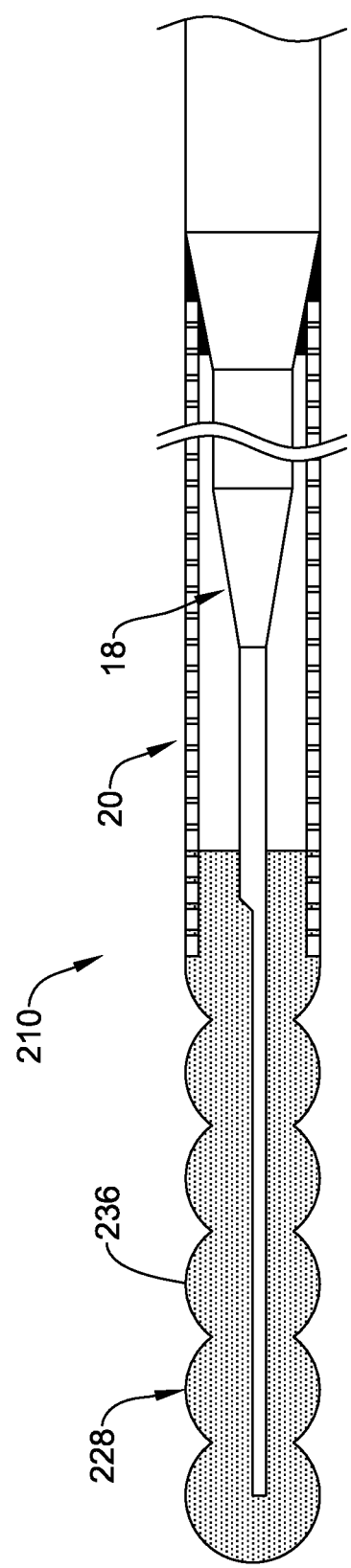
FIG. 4 is a partial cross-sectional side view of another example medical device.

FIG. 4 illustrates another guidewire 210 that may be similar in form and function to other guidewires disclosed herein. Guidewire 210 may include polymeric member 228 having a plurality of circumferential projections 236 formed therein that define an uneven outer surface for polymeric member 228. The cross-sectional view of projections 236 (as shown in FIG. 4) may appear as a series of convex humps or projections. Again, while projections 236 are shown in FIG. 4 as being circumferential, this is not intended to be limiting as guidewires are contemplated that include one or more partially circumferential projections.

Figure 5:
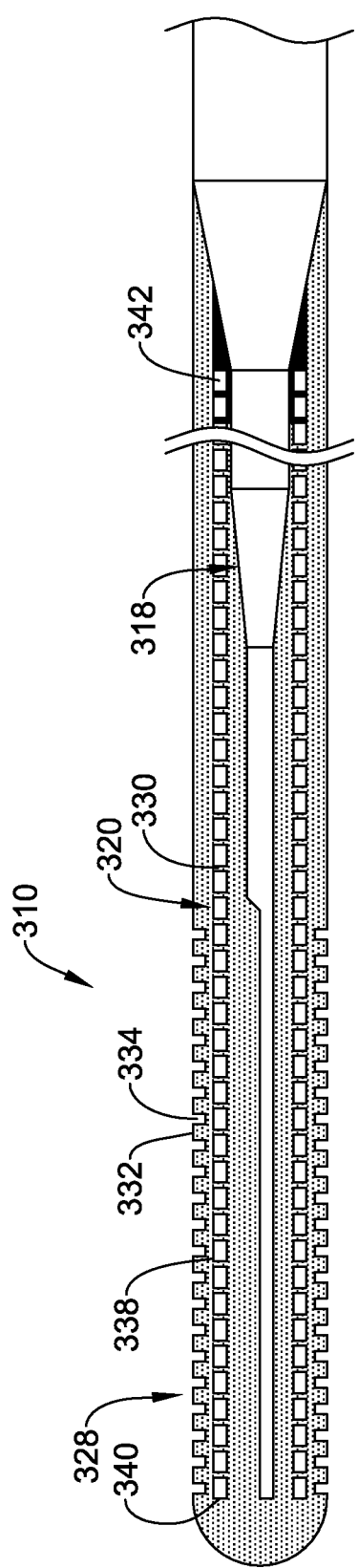
FIG. 5 is a partial cross-sectional side view of another example medical device.

FIG. 5 illustrates another guidewire 310 that may be similar in form and function to other guidewires disclosed herein. Guidewire 310 may include tubular member 320 and core wire 318, which may be similar in form and function to tubular member 20 and core wire 18, respectively. Just like polymeric member 28, polymeric member 328 may have an uneven outer surface 332. In the embodiment illustrated in FIG. 5, uneven outer surface 332 includes cuts or ribs 334 formed therein. Ribs 334 may be similar to ribs 34 disclosed herein.

Polymeric member 328 may be disposed along an outer surface 338 of tubular member 320. Polymeric member 328 may include a lubricious material so as to improve the lubricity of guidewire 310, for example, at its distal tip. In at least some embodiments, ribs 334 may extend to a depth within polymeric member 328 such that a portion of polymeric member 328 extends between the outer surface 338 of tubular member 320 and the inner surface of polymeric member 328. In other embodiments, ribs 334 may extend through polymeric member 328 to the extent that portions of the outer surface 338 of tubular member 320 are not covered by or otherwise do not have polymeric member 328 disposed thereon. The portions of tubular member 320 not covered by polymeric member 328 may or may not include portions of tubular member 320 having slots 330. Along sections of tubular member 320 having slots 330, polymeric member 328 may or may not fill at least some of the slots 330 formed in tubular member 320.

Polymeric member 328 may extend distally beyond a distal end 340 of tubular member 320. For example, polymeric member 328 may extend about 0.1 to 5 centimeters beyond distal end 340 of tubular member 320, or about 0.5 to 3 centimeters beyond distal end 340 of tubular member 320, or about 1 to 2 centimeters beyond distal end 340 of tubular member 320. The portion of polymeric member 328 extending beyond distal end 340 may define a tip of guidewire 310. In addition, polymeric member 328 may extend proximally beyond a proximal end 342 of tubular member 320.

While FIG. 5 illustrates polymeric member 328 as being a solid structure that essentially encapsulates core wire 318 and tubular member 320, this is not intended to be limiting. For example, some embodiments are contemplated where polymeric member 328 is a tubular member that may leave a space or gap between portions of polymeric member 328 and core wire 318. In these embodiments, polymeric member 328 may essentially be disposed along only outer surface 338 of tubular member 320. This may include partially or completely filling some or all of slots 330 formed in tubular member 320. In still other embodiments, polymeric member 328 may be a structure that includes portions that essentially encapsulate core wire 318 and portions are spaced from core wire 318. Numerous alternative variations are contemplated. In one example, a distal portion of polymeric member 328 may encapsulate core wire 318, a middle portion of polymeric member may partially fill or otherwise leave a space between core wire 318 and polymeric member 328 (and/or leave a space between core wire 318 and tubular member 320), and a proximal portion that encapsulates core wire 318 and tubular member 320. The middle portion may also fill or partially fill some of slots 330 formed in tubular member 320. The proximal portion may fill some or all of slots 330 formed in tubular member 320. These are just examples.

Figure 6:
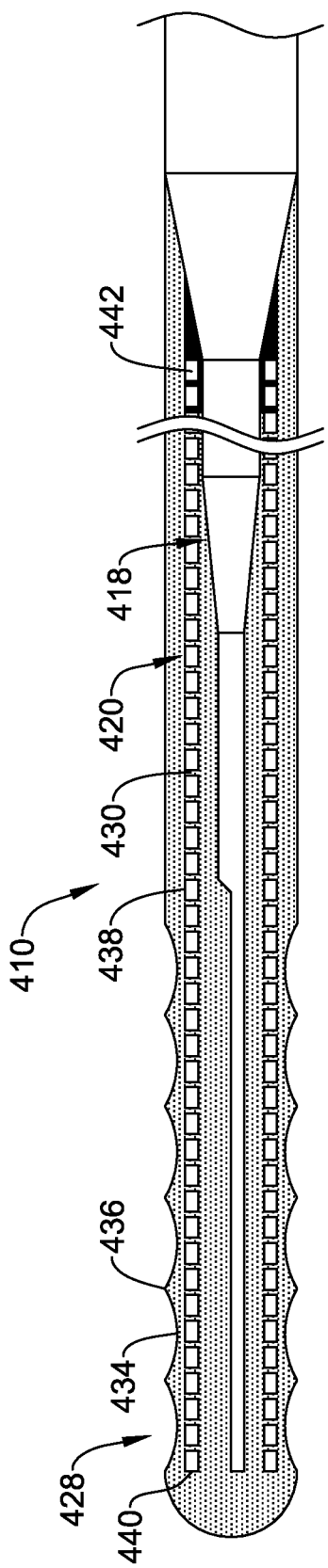
FIG. 6 is a partial cross-sectional side view of another example medical device.

FIG. 6 illustrates another guidewire 410 that may be similar in form and function to other guidewires disclosed herein. Guidewire 410 may include core wire 418 and polymeric member 428 having a plurality of circumferential grooves 434 formed therein. Peaks 436 may be defined between grooves 434. Grooves 434 and peaks 436 may be similar to grooves 134 and peaks 136, respectively.

Polymeric member 428 may be disposed along outer surface 438 of tubular member 420. In at least some embodiments, grooves 434 may extend to a depth such that a portion of polymeric member 428 still remains between the outer surface 438 of tubular member 420 and the inner surface of polymeric member 428. In other embodiments, grooves 434 may extend through polymeric member 428 to the extent that portions of the outer surface 438 of tubular member 420 are not covered by or otherwise do not have polymeric member 428 disposed thereon. The portions of tubular member 420 not covered by polymeric member 428 may or may not include portions of tubular member 420 having slots 430. Polymeric member 428 may or may not fill at least some of the slots 430 formed in tubular member 420.

Polymeric member 428 may extend distally beyond a distal end 440 of tubular member 420. The portion of polymeric member 428 extending beyond distal end 440 may define a tip of guidewire 410. In addition, polymeric member 428 may extend proximally beyond a proximal end 442 of tubular member 420.

Figure 7:
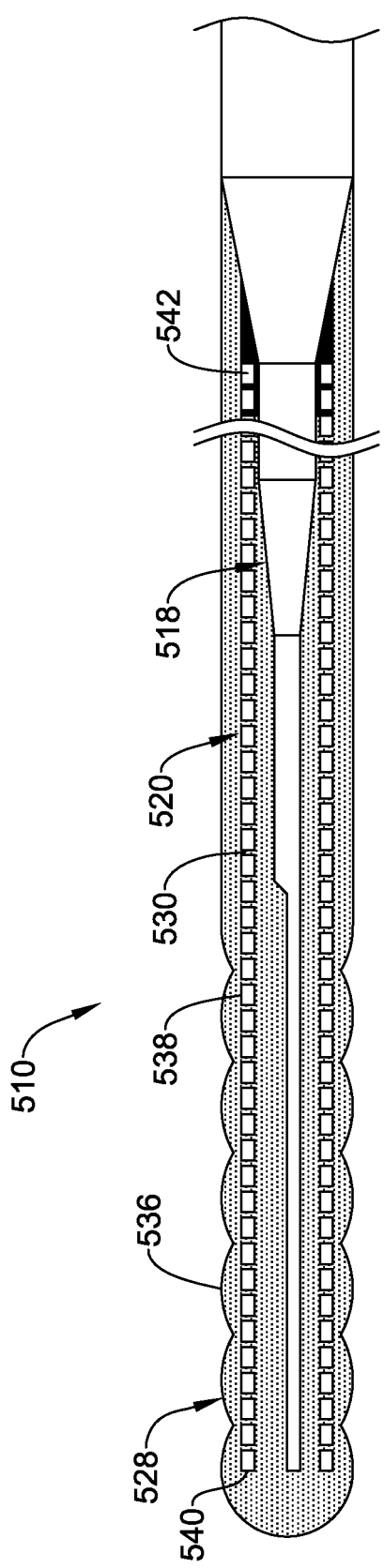
FIG. 7 is a partial cross-sectional side view of another example medical device.

FIG. 7 illustrates another guidewire 510 that may be similar in form and function to other guidewires disclosed herein. Guidewire 510 may include core wire 518 and polymeric member 528 having a plurality of circumferential projections 536 formed therein. Projections 536 may be similar to projections 236 shown in FIG. 4. Polymeric member 528 may be disposed along outer surface 538 of tubular member 520. In at least some embodiments, portions of the outer surface 538 of tubular member 520 may not be covered by or otherwise may not have polymeric member 528 disposed thereon. The portions of tubular member 520 not covered by polymeric member 528 may or may not include portions of tubular member 520 having slots 530. Polymeric member 528 may or may not fill at least some of the slots 530 formed in tubular member 520.

Polymeric member 528 may extend distally beyond a distal end 540 of tubular member 520. The portion of polymeric member 528 extending beyond distal end 540 may define a tip of guidewire 510. In addition, polymeric member 528 may extend proximally beyond a proximal end 542 of tubular member 520.

Various embodiments of arrangements and configurations of slots 30 illustrated in FIG. 1 are contemplated that may be used in addition to what is described above or may be used in alternate embodiments. The same may also be true for the various uneven surfaces for the polymeric members disclosed herein. For the sake of simplicity, the following discussion will be directed primarily to slots 30. However, the discussion may also be applied to the polymeric members disclosed herein. For example, in some embodiments, at least some, if not all of slots 30 are disposed at the same or a similar angle with respect to the longitudinal axis of tubular member 20. As shown, slots 30 can be disposed at an angle that is perpendicular, or substantially perpendicular, and/or can be characterized as being disposed in a plane that is normal to the longitudinal axis of tubular member 20. However, in other embodiments, slots 30 can be disposed at an angle that is not perpendicular, and/or can be characterized as being disposed in a plane that is not normal to the longitudinal axis of tubular member 20. Additionally, a group of one or more slots 30 may be disposed at different angles relative to another group of one or more slots 30. The distribution and/or configuration of slots 30 can also include, to the extent applicable, any of those disclosed in U.S. Pat. Publication No. US 2004/0181174, the entire disclosure of which is herein incorporated by reference.

Slots 30 may be provided to enhance the flexibility of tubular member 20 while still allowing for suitable torque transmission characteristics. Slots 30 may be formed such that one or more rings and/or tube segments interconnected by one or more segments and/or beams that are formed in tubular member 20, and such tube segments and beams may include portions of tubular member 20 that remain after slots 30 are formed in the body of tubular member 20. Such an interconnected structure may act to maintain a relatively high degree of torsional stiffness, while maintaining a desired level of lateral flexibility. In some embodiments, some adjacent slots 30 can be formed such that they include portions that overlap with each other about the circumference of tubular member 20. In other embodiments, some adjacent slots 30 can be disposed such that they do not necessarily overlap with each other, but are disposed in a pattern that provides the desired degree of lateral flexibility.

Additionally, slots 30 can be arranged along the length of, or about the circumference of, tubular member 20 to achieve desired properties. For example, adjacent slots 30, or groups of slots 30, can be arranged in a symmetrical pattern, such as being disposed essentially equally on opposite sides about the circumference of tubular member 20, or can be rotated by an angle relative to each other about the axis of tubular member 20. Additionally, adjacent slots 30, or groups of slots 30, may be equally spaced along the length of tubular member 20, or can be arranged in an increasing or decreasing density pattern, or can be arranged in a non-symmetric or irregular pattern. Other characteristics, such as slot size, slot shape, and/or slot angle with respect to the longitudinal axis of tubular member 20, can also be varied along the length of tubular member 20 in order to vary the flexibility or other properties. In other embodiments, moreover, it is contemplated that the portions of the tubular member, such as a proximal section, or a distal section, or the entire tubular member 20, may not include any such slots 30.

As suggested herein, slots 30 may be formed in groups of two, three, four, five, or more slots 30, which may be located at substantially the same location along the axis of tubular member 20. Alternatively, a single slot 30 may be disposed at some or all of these locations. Within the groups of slots 30, there may be included slots 30 that are equal in size (i.e., span the same circumferential distance around tubular member 20). In some of these as well as other embodiments, at least some slots 30 in a group are unequal in size (i.e., span a different circumferential distance around tubular member 20). Longitudinally adjacent groups of slots 30 may have the same or different configurations. For example, some embodiments of tubular member 20 include slots 30 that are equal in size in a first group and then unequally sized in an adjacent group. It can be appreciated that in groups that have two slots 30 that are equal in size and are symmetrically disposed around the tube circumference, the centroid of the pair of beams (i.e., the portion of tubular member 20 remaining after slots 30 are formed therein) is coincident with the central axis of tubular member 20. Conversely, in groups that have two slots 30 that are unequal in size and whose centroids are directly opposed on the tube circumference, the centroid of the pair of beams can be offset from the central axis of tubular member 20. Some embodiments of tubular member 20 include only slot groups with centroids that are coincident with the central axis of the tubular member 20, only slot groups with centroids that are offset from the central axis of tubular member 20, or slot groups with centroids that are coincident with the central axis of tubular member 20 in a first group and offset from the central axis of tubular member 20 in another group. The amount of offset may vary depending on the depth (or length) of slots 30 and can include other suitable distances.

Slots 30 can be formed by methods such as micro-machining, saw-cutting (e.g., using a diamond grit embedded semiconductor dicing blade), electron discharge machining, grinding, milling, casting, molding, chemically etching or treating, or other known methods, and the like. In some such embodiments, the structure of the tubular member 20 is formed by cutting and/or removing portions of the tube to form slots 30. Some example embodiments of appropriate micromachining methods and other cutting methods, and structures for tubular members including slots and medical devices including tubular members are disclosed in U.S. Pat. Publication Nos. 2003/0069522 and 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing guidewire 10 may include forming slots 30 in tubular member 20 using these or other manufacturing steps.

In at least some embodiments, slots 30 may be formed in tubular member using a laser cutting process. The laser cutting process may include a suitable laser and/or laser cutting apparatus. For example, the laser cutting process may utilize a fiber laser. Utilizing processes like laser cutting may be desirable for a number of reasons. For example, laser cutting processes may allow tubular member 20 to be cut into a number of different cutting patterns in a precisely controlled manner. This may include variations in the slot width, ring width, beam height and/or width, etc. Furthermore, changes to the cutting pattern can be made without the need to replace the cutting instrument (e.g., blade). This may also allow smaller tubes (e.g., having a smaller outer diameter) to be used to form tubular member 20 without being limited by a minimum cutting blade size. Consequently, tubular members 20 may be fabricated for use in neurological devices or other devices where a relatively small size may be desired.

The materials that can be used for the various components of guidewire 10 (and/or other guidewires disclosed herein) and the various tubular members disclosed herein may include those commonly associated with medical devices. For simplicity purposes, the following discussion makes reference to tubular member 20 and other components of guidewire 10. However, this is not intended to limit the devices and methods described herein, as the discussion may be applied to other similar tubular members and/or components of tubular members or devices including the polymeric members disclosed herein.

Tubular member 20 and/or other components of guidewire 10 may be made from a metal, metal alloy, polymer (some examples of which are disclosed herein), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N6625 such as INCONEL® 625, UNS: N6022 such as HASTELLOY® C-22®, UNS: N10276 such as HASTELLOY® C276®, other HASTELLOY® alloys, and the like), nickel-copper alloys (e.g., UNS: N4400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of core wire 18 and/or tubular member 20 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of guidewire 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guidewire 10 to achieve the same result.

In some embodiments, a degree of Magnetic Resonance Imaging (MRI) compatibility is imparted into guidewire 10. For example, to enhance compatibility with MRI machines, it may be desirable to make core wire 18 and/or tubular member 20, or other portions of the guidewire 10, in a manner that would impart a degree of MRI compatibility. For example, core wire 18 and/or tubular member 20, or portions thereof, may be made of a material that does not substantially distort the image and create substantial artifacts (i.e., gaps in the image). Certain ferromagnetic materials, for example, may not be suitable because they may create artifacts in an MRI image. Core wire 18 and/or tubular member 20, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Referring now to core wire 18, the entire core wire 18 can be made of the same material along its length, or in some embodiments, can include portions or sections made of different materials. In some embodiments, the material used to construct core wire 18 is chosen to impart varying flexibility and stiffness characteristics to different portions of core wire 18. For example, proximal section 22 and distal section 24 of core wire 18 may be formed of different materials, for example, materials having different moduli of elasticity, resulting in a difference in flexibility. In some embodiments, the material used to construct proximal section 22 can be relatively stiff for pushability and torqueability, and the material used to construct distal section 24 can be relatively flexible by comparison for better lateral trackability and steerability. For example, proximal section 22 can be formed of straightened 304v stainless steel wire or ribbon and distal section 24 can be formed of a straightened super elastic or linear elastic alloy, for example a nickel-titanium alloy wire or ribbon.

In embodiments where different portions of core wire 18 are made of different materials, the different portions can be connected using a suitable connecting technique and/or with a connector. For example, the different portions of core wire 18 can be connected using welding (including laser welding), soldering, brazing, adhesive, or the like, or combinations thereof. These techniques can be utilized regardless of whether or not a connector is utilized. The connector may include a structure generally suitable for connecting portions of a guidewire. One example of a suitable structure includes a structure such as a hypotube or a coiled wire which has an inside diameter sized appropriately to receive and connect to the ends of the proximal portion and the distal portion. Other suitable configurations and/or structures can be utilized for connector 26 including those connectors described in U.S. Pat. Nos. 6,918,882 and 7,071,197 and/or in U.S. Patent Pub. No. 2006-0122537, the entire disclosures of which are herein incorporated by reference.

In some embodiments, the exterior surface of the guidewire 10 (including, for example, the exterior surface of core wire 18 and/or the exterior surface of tubular member 20 and/or the exterior surface of polymeric member 28) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of core wire 18, tubular member 20, polymeric member 28, or other portions of device 10. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The same may be true of polymeric member 28. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

This application may be relevant to U.S. Patent Application Pub. No. US 2008/0064989, the entire disclosures of which are herein incorporated by reference.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A guidewire, comprising:
   a core wire having a distal portion;
   a non-coiled tubular member disposed over the distal portion, the tubular member having a plurality of slots formed therein; and a polymeric member disposed along an outer surface of the tubular member, the polymeric member having an uneven outer surface with a profile that is independent of a profile of the outer surface of the tubular member and independent of a profile of the core wire.

2. The guidewire of claim 1, wherein the polymeric member includes a polymer doped with a radiopaque material.

3. The guidewire of claim 1, wherein the polymeric member has a plurality of slots formed therein.

4. The guidewire of claim 1, wherein the uneven outer surface of the polymeric member includes a plurality of ribs.

5. The guidewire of claim 1, wherein the uneven outer surface of the polymeric member includes a plurality of circumferential grooves.

6. The guidewire of claim 1, wherein the uneven outer surface of the polymeric member includes a plurality of circumferential projections.

7. The guidewire of claim 1, wherein the core wire includes a flatted distal portion.

8. The guidewire of claim 7, wherein the flattened distal portion is disposed within the polymeric member.

9. The guidewire of claim 1, wherein a portion of the polymeric member extends within the tubular member.

10. The guidewire of claim 1, wherein the polymeric member extends proximally beyond a proximal end of the tubular member.

11. A guidewire, comprising:
a core wire having a distal portion;
a tubular member disposed over the distal portion, the tubular member having a plurality of slots formed therein;
wherein the tubular member includes a longitudinal axis;
wherein the plurality of slots includes at least one pair of opposed slots arranged on opposite sides of the longitudinal axis; and
a polymeric jacket having a first portion disposed along an outer surface of the tubular member and a second portion disposed within the tubular member, the first portion of the polymeric jacket having an uneven outer surface that is independent of the plurality of slots.

12. The guidewire of claim 11, wherein the polymeric jacket includes a polymer doped with a radiopaque material.

13. The guidewire of claim 11, wherein the polymeric jacket has a plurality of slots formed therein.

14. The guidewire of claim 11, wherein the uneven outer surface includes a plurality of ribs.

15. The guidewire of claim 11, wherein the uneven outer surface includes a plurality of circumferential grooves.

16. The guidewire of claim 11, wherein the uneven outer surface includes a plurality of circumferential projections.

17. The guidewire of claim 11, wherein a portion of the polymeric jacket extends proximally beyond a proximal end of the tubular member.

18. A guidewire having an atraumatic distal tip, comprising:
a core wire having a distal portion;
a polymer member disposed over the distal portion;
wherein the polymer member includes a polymer doped with a radiopaque material;
wherein the polymer member forms a distal tip for the guidewire;
wherein the distal tip has an uneven outer surface;
a non-coiled nickel-titanium alloy tubular member disposed over the distal portion of the core wire, the tubular member having a plurality of slots formed therein;
wherein the tubular member includes a longitudinal axis;
wherein the plurality of slots includes at least one pair of opposed slots arranged on opposite sides of the longitudinal axis; and
wherein at least a portion of the polymer member is disposed along an exterior surface of the tubular member and the uneven outer surface includes a plurality of ribs that are offset from the plurality of slots.

* * * * *

UNITED STATES PATENT AND TRADEMARK OFFICE
CERTIFICATE OF CORRECTION

PATENT NO.         : 8,795,202 B2                                      Page 1 of 1
APPLICATION NO.    : 13/365886
DATED              : August 5, 2014
INVENTOR(S)        : Northrop et al.

It is certified that error appears in the above-identified patent and that said Letters Patent is hereby corrected as shown below:

In the Specification:

Column 10
Line 49: before ") to about", delete "."
Line 49: after "to about 120°C", delete "."

Signed and Sealed this
Twenty-first Day of October, 2014

Michelle K. Lee
*Deputy Director of the United States Patent and Trademark Office*